US006334858B1

(12) United States Patent
Rönnberg et al.

(10) Patent No.: US 6,334,858 B1
(45) Date of Patent: Jan. 1, 2002

(54) DIAPER THAT INCLUDES A WAIST BELT AND AN ABSORBENT UNIT

(75) Inventors: Peter Rönnberg; Eva Simmons, both of Mölndal; Anders Gustafsson, Billdal, all of (SE)

(73) Assignee: SCA Molnlycke AB, Gothenburg (SE)

( * ) Notice: Subject to any disclaimer, the term of this patent is extended or adjusted under 35 U.S.C. 154(b) by 0 days.

(21) Appl. No.: 09/380,306

(22) PCT Filed: Feb. 11, 1998

(86) PCT No.: PCT/SE98/00234

§ 371 Date: Sep. 30, 1999

§ 102(e) Date: Sep. 30, 1999

(87) PCT Pub. No.: WO98/37847

PCT Pub. Date: Sep. 3, 1998

(30) Foreign Application Priority Data

Feb. 28, 1997 (SE) ................................ 9700731

(51) Int. Cl.⁷ ................................................. A61F 13/15
(52) U.S. Cl. ...................... 604/392; 604/396; 604/398
(58) Field of Search ....................... 604/385.01, 385.13, 604/385.21, 385.23, 386, 387, 391, 392, 393, 396, 397, 398

(56) References Cited

U.S. PATENT DOCUMENTS

| 5,445,628 A | * | 8/1995 | Gipson et al. | 604/392 |
| 5,482,755 A | * | 1/1996 | Manning | 428/95 |
| 5,549,593 A | * | 8/1996 | Ygge et al. | 604/391 |
| 5,611,789 A | * | 3/1997 | Seth | 604/391 |
| 5,662,636 A | * | 9/1997 | Benjamin et al. | 604/385.2 |
| 5,725,518 A | * | 3/1998 | Coates | 604/391 |
| 5,971,970 A | * | 10/1999 | Carlbark et al. | 604/385.2 |

FOREIGN PATENT DOCUMENTS

| EP | 0 409 307 | 1/1991 |
| GB | 2 266 055 | 10/1993 |
| WO | WO 90/08524 | 8/1990 |
| WO | WO 91/08725 | 6/1991 |

* cited by examiner

*Primary Examiner*—John G. Weiss
*Assistant Examiner*—Jamisue Webb
(74) *Attorney, Agent, or Firm*—Young & Thompson

(57) ABSTRACT

A diaper or incontinence guard includes a waist belt (1) and an absorbent unit (2) with a front part (3), a rear part (4) and an intermediate crotch part (5). Fastener devices (9–11 and 6–8 respectively) are disposed at the front end and the rear end of the absorbent unit and can be fastened to the belt. Each of the front and rear ends of the absorbent unit (2) includes a respective central fastener device (10 and 7) that is located on the longitudinal symmetry axis (A—A) of the unit, and two lateral fastener devices (9, 11 and 6, 8 respectively) located on respective sides of the axis.

7 Claims, 2 Drawing Sheets

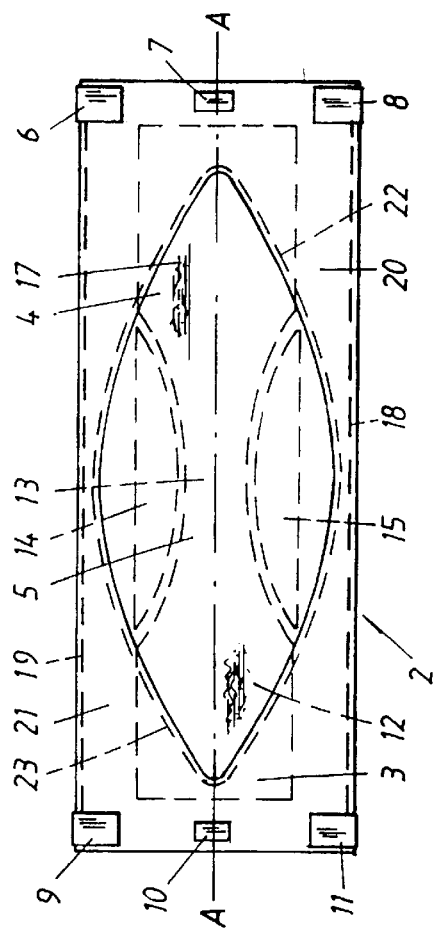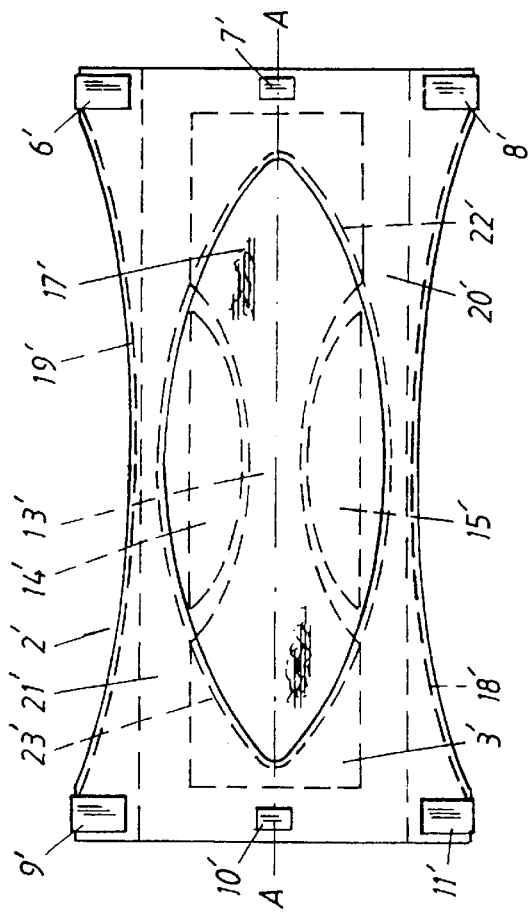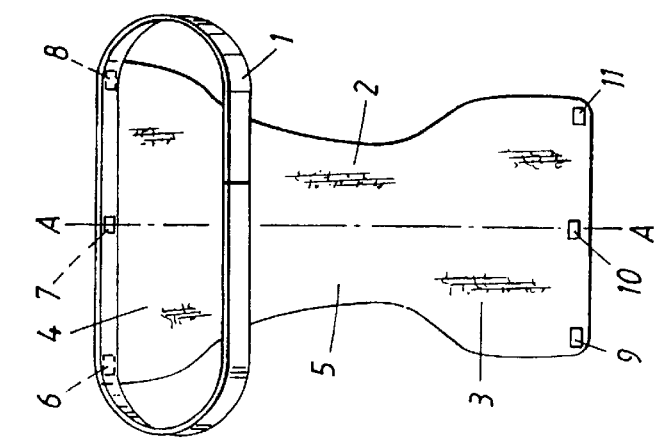

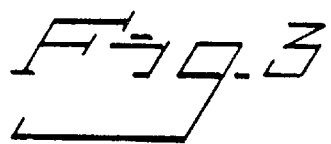
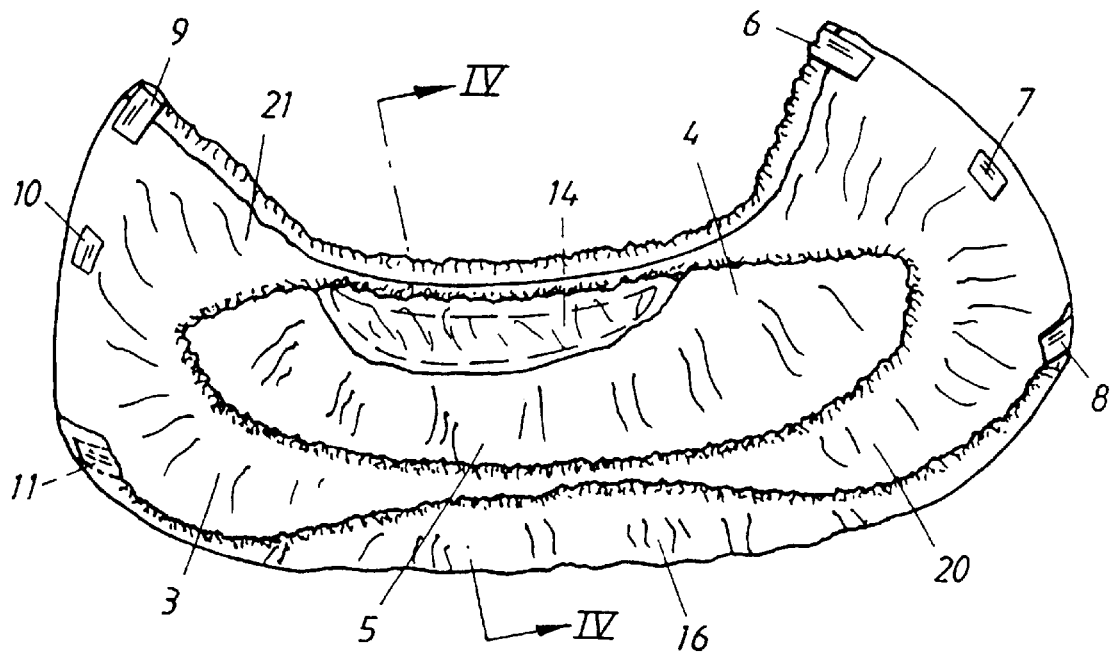
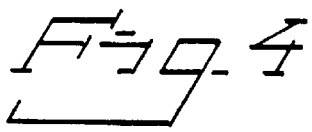
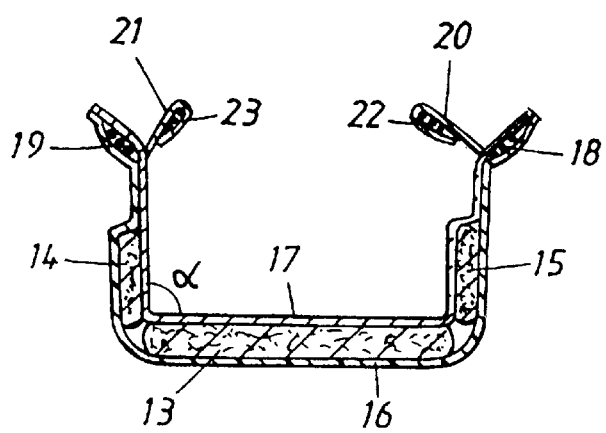

DIAPER THAT INCLUDES A WAIST BELT AND AN ABSORBENT UNIT

CROSS REFERENCE TO RELATED APPLICATION

This is the 35 USC 371 national stage of international application PCT/SE98/00234 filed on Feb. 11, 1998, which designated the United States of America.

FIELD OF THE INVENTION

The present invention relates to a diaper that includes a waist belt and an absorbent unit having a front part, a rear part and an intermediate crotch part, and fastener devices provided in the front and the rear end of the absorbent unit, said fastening devices being fastenable to the belt.

BACKGROUND OF THE INVENTION

Such diapers are primarily intended for use as adult diapers or incontinence guards and shall be capable of being applied to a diaper user with said user in a recumbent position. In applications such as these, it is difficult to position the diaper correctly, and it may therefore be necessary to move a bed-lying user several times before the diaper is positioned correctly. In the case of modern diapers, it is important to apply the diapers correctly in order to be able to fully utilize their absorption and sealing properties. It is also important that the fastener devices are constructed to enable the diaper to be held in position even when the absorbent body is saturated or almost saturated and therewith much heavier than when dry.

SUMMARY OF THE INVENTION

The object of the present invention is to solve these problems.

This object is achieved in accordance with the invention with a diaper of the aforedescribed kind which is characterized in that the front and rear end of the absorbent unit each include a centre fastener device which is positioned on the longitudinal symmetry axis of the unit, and two lateral fastener devices which are positioned on respective sides of said axis. The centre fastener device enables the diaper to be applied in the correct position very easily at the first attempt, since the spine and navel provide natural reference points when applying the diaper. When the centre fastening devices are applied first when putting on the diaper, the lateral fastener devices can be fastened correctly independently of one another, therewith enabling a diaper to be put onto a user lying on one side, without risk of needing to make any subsequent adjustment. Furthermore, the central suspension of the diaper reduces the risk of the absorbent unit of an applied diaper being moved out of position by externally acting forces when the diaper is in use. The central suspension also ensures that the longitudinally extending elastic elements normally found in diapers will be stretched or tensioned to mutually the same extent when applying the diaper. It also ensures that the central parts of the diaper will not sag in use, due to the greater weight of the diaper after having absorbed liquid.

In one preferred embodiment of the invention, the fastener devices of the absorbent unit have the form of hooks and the waist belt is provided on its outer surface with a loop-material into which the hooks on the fastener devices can engage. The loop-material may conveniently consist of a nonwoven fabric, or a velour fabric. Other knitted or woven textile materials are also suitable for use as said loop material. The loop material will preferably cover the whole of the outer surface of the belt. The absorbent unit includes an absorbent body enclosed between an outer, liquid-impermeable casing sheet and an inner, liquid-permeable casing sheet, and longitudinally extending side flaps which extend on respective sides of the longitudinal symmetry axis from the side-edge parts of the unit and in over the inner casing sheet, and which include longitudinally extending elastic elements along their edges that face towards said axis.

BRIEF DESCRIPTION OF THE DRAWINGS

The invention will now be described with reference to the accompanying drawings, in which FIG. 1 illustrates schematically a partially assembled diaper according to a first embodiment of the invention;

FIG. 2 shows a top plan view of the absorbent unit included in the schematically illustrated diaper of FIG. 1;

FIG. 3 is a perspective view of the absorbent unit shown in FIG. 2;

FIG. 4 is a sectional view taken on the line IV—IV in FIG. 3; and

FIG. 5 is a view similar to FIG. 2 that shows an absorbent unit according to a second embodiment of the invention.

DESCRIPTION OF THE PREFERRED EMBODIMENTS

FIG. 1 is a highly schematic illustration of an inventive diaper or incontinence guard. The diaper is comprised of two separate parts, i.e. a waist belt 1 and an absorbent unit 2. The absorbent unit 2 has a front part 3, a rear part 4 and an intermediate crotch part 5. The fastener devices 6–11 are disposed along respective front and rear end-edges of said unit 2, on that side of the unit which faces towards the wearer's body in use. A centre fastener device 7 and a centre fastener device 10 is provided on a respective end-edge, wherewith an imaginary longitudinal symmetry axis A—A of the unit extends through the centre point of respective centre fastener devices. Fastener devices 6, 8 and 9, 11 are provided on respective sides of said centre fastener devices 7, 10 in the corners of the unit.

The whole of the outside of the waist belt 1, i.e. that side of the belt which lies distal to the wearer's body in use, is covered with a material to which the fastener devices 6–11 can be fastened, released and refastened. The fastener devices may be hooked elements of the touch-and-close type that coact with a suitable loop material on the waist belt. A suitable material having hook-like projections that can fasten to textile materials or textile-like materials is CS200 from the American company 3M. Naturally, the use of adhesive tapes that coact with a suitable plastic material on the belt to provide a releasable and refastenable suspension of the diaper unit 2 from the belt 1 are also conceivable. The waist belt may consist entirely of a material to which the fastener devices can be fastened. Alternatively, the waist belt may be made of a carrier material whose inner surface is covered with a skin-friendly material and the outer surface of which is provided with a covering of the aforesaid kind. When the material coacting with the fastener devices is skin-friendly, the same material can be used to cover both the inside and the outside of the waist belt. The waist belt may alternatively comprise two-ply layers and consist of spunbond nonwoven material and a loop material, e.g. a nonwoven material or velour fabric. The waist belt will, of course, include means that enable it to be fastened to itself at an overlap, said overlap being sufficient to accommodate users of different waist sizes within the framework of the category of user for which the diaper is intended.

FIG. 1 shows the diaper with the rear edge of the unit 2 fastened to the waist belt 1 fitted around the waist of a standing diaper carrier (not shown). When securing the fastener devices, the centre fastener device 7 is suitable fastened first, so that said fastener lies across the wearer's spine. The fastener devices 6, 8 are then secured. The front part 3 of the unit 2 is then pulled between the wearer's thighs and the fastener device 10 firmly pressed onto the waist belt, such that an extension of the longitudinal symmetry axis A—A of the unit 2 passes beyond the wearer's navel. The fastener devices 9, 11 are then affixed to the belt.

The diaper illustrated in FIG. 1 can also be applied to a diaper carrier with the carrier lying on one side. When the belt 1 has been placed around the carrier, the centre fastener device 7 of the unit 2 is fastened across the carrier's spine. The lateral fastener device of the unit 2, which is to be fastened to the upwardly directed part of the belt carried by the carrier, can then be applied with the upwardly directed half of the rear end-edge of the unit 2 extended or stretched, without risk of the diaper unit being moved laterally in its entirety as the end-edge is stretched. The front part of the diaper unit is then brought between the user's thighs and the centre fastener device on the front end-edge is fastened to the waist belt. The upwardly extending half of the front end-edges of the unit 2 can then be applied. When this has been done, the diaper carrier is turned so that the other side faces upwards and the nonfastened fastener devices on the front and the rear end-edges are fastened to the belt. Because it has been ensured that the previously attached fastener devices have been applied correctly, stretching of the front and the rear end-edge prior to fastening said fastener devices will bring said fastening devices to their correct positions. A diaper that has been fitted to a diaper carrier in this way will require no subsequent adjustment, as is often necessary in the case of similar diaper units that lack centre fastener devices.

A preferred embodiment of a diaper unit 2 is shown in more detail in FIGS. 2–4. FIG. 2 shows the diaper unit in a flat state, i.e. with the elastic elements stretched, the diaper unit being held in this state during manufacture and prior to being packeted. FIGS. 3 and 4 show the diaper unit in a relaxed state, i.e. the state that the diaper unit has after being removed from its packet and before being placed on a diaper carrier.

The illustrated diaper unit includes an absorbent body 12, which is divided into a main part 13 and two side-parts 14, 15 that are separated from the main part by folding indications?. The folding indications are curved so that the main part 13 obtains an hourglass configuration. The absorbent body 12 is comprised of air-lain cellulose fluff, although it may, of course, be made of any absorbent material of the kind used in absorbent bodies for diapers or incontinence guards. The absorbent body may be comprised of one or more layers and may contain so-called superabsorbents or not.

The absorbent body 12 is conventionally enclosed between an outer liquid-impermeable casing sheet 16, made of polyethylene plastic for instance, and an inner liquid-permeable casing sheet, which is preferably comprised of nonwoven fabric. The outer and inner casing sheets may, of course, be comprised of material other than polyethylene and nonwoven respectively. The casing sheets 16, 17 extend beyond the absorbent body 12 around the whole of its perimeter and are joined together at those parts that lie outside the absorbent body.

In the case of the illustrated embodiment, the folding indications between the side-parts 14, 15 and the main part 13 of the absorbent body are provided by separating the parts 14, 15 from the main part 13 with the aid of a gap in which the casing sheets 16, 17 are joined together. The folding indications can, of course, be provided in other ways, e.g. with the aid of compression strings.

Elastic elements 18, 19 extend along the respective long edges of the diaper unit. As will be evident from FIG. 4, the elastic elements 18, 19 of the illustrated embodiment comprise three prestretched elastic threads that are mounted between the casing sheets 16, 17 and fastened thereto. Naturally, elastic ribbons or like devices can be used instead of threads and the number of elastic elements used may vary.

Flexible flaps 20, 21 are disposed longitudinally along the long edges of the diaper unit. These flaps are fastened to the casing sheets 16, 17 along the longitudinal edges of the unit and extend in over the inner casing sheet 17. The flaps 20, 21 have a narrowest part in the crotch-part 5 and extend from a point in said crotch-part towards the front-part 3 and the rear-part 4 respectively with a successively increasing width in towards the longitudinal symmetry axis A—A of the diaper unit. In the illustrated embodiment, the flaps 20, 21 extend up to the longitudinal symmetry axis A—A at points slightly inwards of the front and rear parts respectively and extend from these points at a constant width up to the front and rear ends of the diaper unit respectively. The flaps in these regions of constant width are joined together and therewith form a perforated top sheet. The elastic threads or elastic tapes 22, 23 are fastened to the flaps 20, 21 along the curved sections of their inner long edges.

All of the elastic elements 18, 19, 22 and 23 are mounted in a prestretched or extended state. These elements will thus strive to contract from their prestretched state to a relaxed state. When no load is exerted on the diaper unit, for instance in the case of a diaper unit removed from its package, the elastic elements 18, 19, 22, 23 will contract and therewith pucker the pliable sheets 16, 17, 20, 21 to which they are attached. As the flaps 20, 21 contract, the main-part 13 of the absorbent body 12 will curve and, at the same time, the side-parts 14, 15 of the absorbent body and those parts of the casing sheets 16, 17 that lie outside the main-part 13 of said body will fold upwards, i.e. such that those parts of the inner casing sheet that cover the inside of the side-parts 14, 15 will face towards each other. The stiffness or rigidity of the absorbent body 12 is such that the spring force exerted by the elastic elements will essentially only deform the body 1 by bending. This can readily be achieved by suitable compression of a cellulose fluff body or with the aid of a multi-layer body having a bottom layer of stiffer material, which may be absorbent or not.

FIGS. 3 and 4 show the diaper unit of FIG. 2 in a relaxed state. As will be evident from these Figures, contraction of the flaps 20, 21 and associated bending or curving of the main-part 13 of the absorbent body 12 causes the top sheet formed by said flaps to extend above and at a distance from the absorption body 12. When the diaper unit is donned, the unit will be stretched somewhat from the state shown in FIGS. 3 and 4, therewith increasing the spring force in the elastic elements. When the diaper unit is donned, the elastic elements will urge the curved edges of the flaps 20, 21 resiliently against the wearer's body and the long edges of the diaper unit against the wearer's thighs. The major part of the bend or curve in the main-part 13 of the absorbent body will, however, remain when the diaper is donned, said main-part 13 therewith being located at a distance from the wearer's body in addition to at the ends of said part.

FIG. 4 is a cross-sectional view of the diaper unit in FIG. 3, taken through the narrowest section of the main-part 13 of the absorbent body 12 in the crotch part of the diaper. In this narrowest section, the main-part 13 of the absorbent body is located furthest from the flaps 20, 21. In order to enable the side-parts 14, 15 to be folded-up perpendicular to the plane of said main-part without deforming the main-part or the side-parts, the folding indications shall have a width which is equal to or greater than √2? times the thickness of the absorbent body 12. When the width of the wearer's crotch coincides with the width of the main-part 13, the diaper unit will retain this configuration when donned. The main-part 13 is dimensioned for a mean crotch width value for the category of user for which the diaper unit is intended. The crotch width of small children is normally from 3 to 4 cm, and for adults from 4–7 cm. Consequently, the angle α between the main-part 13 of the absorbent body and the side-parts 14, 15 of a donned diaper unit will only deviate from a right angle of a standing user to a relatively small extent. However, larger angular deviations may occur as the wearer moves his/her legs. In order to be sure that discharged liquid will always have access to the space between main-part 13 and flaps 20, 21 without obstruction from the flaps, the flaps must not be too wide in the crotch-part of the wearer. The flaps will preferably not have a greater width than 2 cm at the position of the smallest section of the main-part 13 of the absorbent part 12 in the crotch-part.

It has been found that the narrowest section of the main-part of the absorbent body located in the crotch part will have preferably a greatest width corresponding to 60% of the total width of the diaper in this section thereof, so that the main-part is able to bend conveniently while being held spaced from the wearer's body over a greater part of its length.

In addition to keeping the main-part 13 of the absorbent body 12 spaced from the wearer's body, the elastic elements 22, 23 in the flaps 20, 21 also function to press sealingly against the wearer's body so as to prevent urine or faces contacting that side of the flaps which lie against the wearer's body. It has been found that a good sealing function is achieved, when the elastic elements of the flaps in the crotch region are located in the wearer's groins. This positioning of the elastic elements prevents sideways movement of the flaps in the crotch region, irrespective of the external forces to which the diaper unit may be subjected as the wearer moves. The leg elastic 18, 19 shall also be located in the proximity of the wearer's groins in order to obtain an optimal sealing function. In order to make such application of the elastic elements 18, 19, 22, 23 possible, the smallest distance between the outer limitations of the leg elastic 18, 19 and the inner limitations of adjacent flap elastic 22 and 23 respectively shall not exceed 3.5 cm when the diaper unit is held flat. Thus, this configuration of the leg and flap elastic respectively provides a double sealing function against lateral leakage at the narrowest part of the diaper unit.

When large quantities of liquid are discharged at one and the same time, as is often the case with adult wearers, the absorbent body is unable to absorb all of this liquid at once and some of the liquid will run along the inner casing sheet towards the lowest part of the diaper unit. Consequently, when the wearer lies on his/her side there is a risk of liquid collecting at the long edge of the front or the rear part of the diaper unit. Consequently, when the flaps are narrow in these parts of the diaper unit, there is a risk of liquid running over the edges of the flaps and out over said flaps. In order to greatly reduce this risk, the flaps 20, 21 have their greatest width in these parts.

FIG. 5 illustrates a second embodiment of an inventive diaper unit. The only difference between the diaper unit shown in FIG. 5 and the diaper unit shown in FIGS. 2–4 is that the flaps 20', 21' of the FIG. 5 embodiment have parts that extend beyond the longitudinal edges of the casing sheets and that the leg elastic 18', 19' extends in these parts, and that the fastener devices 6', 7', 8', 9', 10', 11' are fastened in said parts. The diaper unit is constructed in other respects in the same way as the aforedescribed diaper units and those components that find correspondence in the embodiment illustrated in FIGS. 2–4 have been designated the same reference signs in FIG. 5, with the addition of a prime, such as 13', 14', 15', 17', 22' and 23'. Such an arrangement is beneficial from the aspect of manufacture, since all elastic elements are disposed on one single sheet that can be applied to the remainder of the diaper unit in a final stage of manufacture.

The flaps are made of a skin-friendly material, which may be liquid-permeable or not. The material from which the flaps are made will preferably be air-permeable. An SMS material, i.e. a three-ply nonwoven material that includes a layer of meltblown-nonwoven between two layers of spunbond-nonwoven is one example of a suitable material in this regard. Examples of other materials conceivable for use as flap material are hydrophobic, spunbond-nonwoven materials.

As a result of the central suspension of the diaper unit in the waist belt achieved by means of the centre fastener devices 7, 10, the elastic elements in the flaps will be tensioned or stretched uniformly when the diaper unit is donned and will retain this tension whilst the diaper is in use. The inner edges of the flaps will thus retain their positions, irrespective of external forces on the diaper. The central suspension also prevents the diaper unit sagging between the corner-located suspension points when the absorbent body has absorbed liquid and therewith become heavier and change the positions of the flaps relative to the wearer's body and the tension in the elastic elements in the flaps. In addition to enabling the diaper unit to be positioned correctly on a wearer, the central suspension also contributes to retaining the intended position during use, so that the diaper will function in the manner intended.

Although the described diaper, or napkin, is intended primarily for adult wearers, its principle construction can be applied advantageously for diapers for small children.

It will be understood that the aforedescribed embodiment of the invention can be modified within the scope of the invention. For example, diaper units of simpler construction than those described may be used. Furthermore, the fastener devices need not be fastenable to the waist belt along the whole of its length. It may, for instance, be desirable to design the belt with elastic parts at those portions which are intended to extend or stretch over a wearer's hips. Fastener devices other than touch-and-close fasteners and adhesive tapes may be used, for instance press studs or like fastener devices comprised of male and female elements. The invention is therefore restricted solely by the contents of the following claims.

What is claimed is:

1. An absorbent garment comprising:
    a waist belt having an outer surface;
    an absorbent unit comprising a front part, a rear part, and an intermediate crotch part, and having a longitudinal symmetrical axis extending through said front, rear and crotch parts;

said absorbent unit having opposite longitudinal ends;

each of said opposite longitudinal ends comprising a central fastener on said longitudinal symmetrical axis and two fasteners spaced laterally from said central fastener adjacent to respective opposite lateral edges of said longitudinal ends; and said fasteners adapted to fasten said absorbent unit to said waist belt, and being disposed on a side of the absorbent unit, which in use faces towards a wearer.

2. The absorbent garment according to claim 1, wherein the fasteners comprise hook elements, and the waist belt has on its outer surface a loop material for fastening said hook elements.

3. The absorbent garment according to claim 2, wherein the loop material is a non-woven fabric.

4. The absorbent garment according to claim 2, wherein the loop material i s a knitted or woven fabric.

5. The absorbent garment according to claim 2, wherein the loop material is a velour fabric.

6. The absorbent garment according to claim 2, wherein the loop material covers the entire outer surface of said waist belt.

7. The absorbent garment according to claim 1, wherein the absorbent unit includes an absorbent body enclosed between an outer liquid-impermeable casing sheet, and an inner liquid-permeable casing sheet, and longitudinally extending side flaps which extend on respective sides of the longitudinal symmetrical axis from side edge parts of said absorbent unit in over the inner casing sheet, and which include longitudinally extending elastic elements along inner longitudinal edges of said side flaps that face towards the longitudinal symmetrical axis.

* * * * *